(12) United States Patent
Fowler, Jr.

(10) Patent No.: US 6,190,312 B1
(45) Date of Patent: Feb. 20, 2001

(54) VARIABLE GEOMETRY RETRACTOR AND DISPOSABLE RETRACTOR STAY CLIPS AND METHOD OF USE

(75) Inventor: James M. Fowler, Jr., Houston, TX (US)

(73) Assignee: Lone Star Medical Products, Inc., Houston, TX (US)

( * ) Notice: Under 35 U.S.C. 154(b), the term of this patent shall be extended for 0 days.

(21) Appl. No.: 09/262,955

(22) Filed: Mar. 4, 1999

(51) Int. Cl.$^7$ .......................................... A61B 1/32

(52) U.S. Cl. .......................................... 600/231; 600/233

(58) Field of Search .................... 600/227, 231, 600/232, 233, 234, 217

(56) References Cited

U.S. PATENT DOCUMENTS

| | | |
|---|---|---|
| Re. 32,021 | 11/1985 | Scott, Jr. . |
| 170,573 | 11/1875 | Lesh .................... 24/300 X |
| 334,711 | 1/1886 | Lorenz .................... 24/265 EE X |
| 2,701,562 * | 2/1955 | Michael et al. .................... 600/217 |
| 3,040,739 * | 6/1962 | Grieshaber .................... 600/234 X |
| 3,515,129 | 6/1970 | Truhan . |
| 3,542,015 | 11/1970 | Steinman . |
| 3,655,964 | 4/1972 | Slight .................... 250/43.5 D |
| 3,749,088 | 7/1973 | Kohlmann . |
| 3,762,401 | 10/1973 | Tupper . |
| 3,916,879 | 11/1975 | Cotten . |
| 4,048,987 | 9/1977 | Hurson . |
| 4,099,521 * | 7/1978 | Nestor et al. .................... 600/231 X |
| 4,185,636 | 1/1980 | Gabbay et al. .................... 128/334 R |
| 4,190,042 | 2/1980 | Sinnreich . |
| 4,254,763 | 3/1981 | McCready et al. . |
| 4,257,406 | 3/1981 | Schenk . |
| 4,263,900 | 4/1981 | Nicholson . |
| 4,274,398 | 6/1981 | Scott, Jr. . |
| 4,321,916 | 3/1982 | McKee . |
| 4,337,762 | 7/1982 | Gauthier . |
| 4,337,763 | 7/1982 | Petrassevich . |
| 4,344,420 | 8/1982 | Forder . |
| 4,355,631 | 10/1982 | LeVahn . |
| 4,380,999 | 4/1983 | Healy . |
| 4,387,706 | 6/1983 | Glass . |
| 4,412,532 | 11/1983 | Anthony . |
| 4,421,107 | 12/1983 | Estes et al. . |
| 4,421,108 | 12/1983 | Cabrera et al. . |
| 4,430,947 | 2/1984 | Kvame .................... 108/111 |
| 4,430,984 | 2/1984 | Tharman .................... 123/647 |

(List continued on next page.)

FOREIGN PATENT DOCUMENTS

| | | | |
|---|---|---|---|
| 3234875 * | 3/1984 | (DE) .................... | 600/233 |
| 1222141 | 2/1971 | (GB) . | |
| 1550254 | 8/1979 | (GB) . | |
| 1550255 | 8/1979 | (GB) . | |

OTHER PUBLICATIONS

Bone Retractors and Retractors AESCULAP®, Product catalog, p. 319 (2 pages) (no date).

*Thermoplastic Replaces Metal in Disposable Abdominal Retractor*, MD&M Review, ULTOP® Conveyor Modules (no date).

I.S.I. North America, Inc. *International Surgical Instruments* __Brochure (no date).

*Accurate Surgical & Scientific Instruments Corporation* Brochure, p. 39 (no date).

Primary Examiner—Jeffrey A. Smith
(74) Attorney, Agent, or Firm—Akin, Gump, Strauss, Hauer & Feld, L.L.P.

(57) ABSTRACT

An improved surgical retractor stay system has a variable geometry retractor frame and disposable retractor stay clips. The retractor stay clips are adapted to snap onto the variable geometry retractor frame and are slidably movable thereon. The retractor frames are custom made having variable geometry and are prepared from extruded metals. The surgical retractor stay system uses the snap-on retractor stay clips in conjunction with the variable geometry retractor frame.

32 Claims, 5 Drawing Sheets

OTHER PUBLICATIONS

| | | |
|---|---|---|
| 4,430,991 | 2/1984 | Darnell . |
| 4,434,791 | 3/1984 | Darnell . |
| 4,559,677 | 12/1985 | Tracy ........................................ 24/300 |
| 4,685,467 | 8/1987 | Cartmell et al. ...................... 128/640 |
| 4,852,312 | 8/1989 | Harbom .............................. 52/126.3 |
| 5,080,088 | 1/1992 | LeVahn . |
| 5,141,973 | 8/1992 | Kobayaski et al. .................. 523/300 |
| 5,231,974 | 8/1993 | Giglio et al. . |
| 5,233,720 | 8/1993 | Schon ................................ 15/250.31 |
| 5,260,576 | 11/1993 | Sommer, Jr. et al. ............ 250/359.1 |
| 5,307,805 | 5/1994 | Byrne . |
| 5,337,736 | 8/1994 | Reddy . |
| 5,518,124 | 5/1996 | Sommer, Jr. et al. ................ 209/577 |
| 5,738,224 | 4/1998 | Sommer, Jr. et al. ................ 209/588 |
| 5,769,783 | 6/1998 | Fowler, Jr. ........................... 600/226 |
| 5,785,649 | 7/1998 | Fowler, Jr. ........................... 600/233 |
| 5,899,853 * | 5/1999 | Fowler, Jr. ........................... 600/217 |
| 5,951,467 * | 9/1999 | Picha et al. ......................... 600/233 |
| 5,964,697 * | 10/1999 | Fowler, Jr. ...................... 600/217 X |
| 5,964,698 * | 10/1999 | Fowler ................................ 600/217 |
| 6,077,221 * | 6/2000 | Fowler, Jr. ........................... 600/233 |

* cited by examiner

VARIABLE GEOMETRY RETRACTOR AND DISPOSABLE RETRACTOR STAY CLIPS AND METHOD OF USE

BACKGROUND OF THE INVENTION

1. Field of the Invention

The present invention relates to surgical retractors and surgical retractor stays. More particularly, the present invention relates to a variable geometry retractor frame and a snap-on clip for receiving and securing an end portion of an elastic member of a surgical retractor stay wherein the snap-on clip is slidably movable on the surgical retractor frame, is removably detachable from the surgical retractor frame and is disposable.

2. Description of the Related Art

During the course of a surgical procedure or operation, the surgeon opens the patient with a scalpel, forming an incision and surgical site. As the surgeon cuts deeper, the operating room staff typically holds tissue away from the operative field using retractors.

Most retractors are one piece metallic implements that retract a wound in a non-yielding manner. Manipulation and movement of the surgeon as well as movement caused by contracting muscles or tissues of the patient can result in bruising or tearing of tissue.

Once an incision is separated and retracted, there is often a need for multiple stays in the form of sutures for holding various tissues, for example different organs. Elastic surgical retractor systems are in commercial use that include elastic stays, each having an elongated elastic member that is typically a hollow length of elastic tubing. The elastic tubing provides proximal and distal end portions. The distal end portion carries an elongated hook constructed of wire.

The wire hook has a proximal end that is placed in the distal end of the bore of the hollow tubing. A shrink wrap is placed over the hook and tubing to hold the proximal end of the wire hook firmly in position within the bore of the tubing at the distal end. The embedded portion of the wire hook member is usually recurved or folded. This folded proximal portion of the wire hook expands the tubing slightly, forming a vertically extended portion that defines a handle.

Various patents have issued for elastic stay retractor systems. A surgical retractor array system is disclosed in U.S. Pat. No. 4,434,791, issued to W. Dale Darnell on Mar. 6, 1984. This surgical retractor system comprises an array of standardized, interchangeable, annular retractor frame sections of various shapes of which the end portions are configured to permit the interchangeable, hinged connection of the various shaped frames in forming generally annular retractor units adaptable to conform to fit the surface contours of various patients upon which a surgical operation is to be performed. This retractor frame is designed to accept yielding rubber or like elastic stays.

Other recent patents have issued that relate to elastic type retractor stays and related retractor frames and systems.

U.S. Pat. No. 4,274,398, issued to Frank B. Scott, Jr., issued Jun. 23, 1981, discloses a surgical retractor which includes an annular frame conformed to fit the surface contour of the portion of the body to be operated on. At least one stay includes an elastic member and a tissue holding hook. The frame has a plurality of notches spaced about its periphery. The elastic portion of the stay is in the form of a length of hollow elastic tubing adapted to be inserted into one of the notches of the frame and held in place by friction to retract the tissue. The hook is a single, curved wire member. It has a folded proximal end that fits the hollow bore of the elastic tube.

SUMMARY OF THE INVENTION

A system according to the present invention provides a variety of features, including a variable geometry retractor system having a variable geometry retractor frame and disposable, snap-on retractor stay clips.

One embodiment according to the present invention provides a snap-on clip with an arc-shaped end and knob, extension or protrusion defining a recess adapted to receive a tubular or cylindrical retractor frame such as a variable geometry retractor frame. Another embodiment according to this invention provides a snap-on clip having a recess adapted to receive a substantially rectangular variable geometry retractor frame having parallel indented tracks on the sides for engaging a securing lip of the snap-on clip.

One embodiment according to the present invention provides a tubular or cylindrical retractor frame for receiving the snap-on clip having an arc shaped end. Another embodiment according to this invention provides a substantially rectangular frame having parallel indented tracks on the sides of the frame for engaging a securing lip of the snap-on clip.

One embodiment according to the present invention provides for an elongated substantially cylindrical coupler for receiving and securing portions of a cylindrical variable geometry retractor frame. Another embodiment according to the present invention provides for a generally rectangular coupler for receiving and securing portions of the generally rectangular retractor frame.

One embodiment according to the present invention provides for a variable geometry retractor frame having end portions angled or bent relative to the plane of the middle portion of the frame. The angled end portions may have a plurality of bends.

One embodiment according to the present invention provides a snap-on clip having an aperture for receiving an elastic member of a surgical retractor stay and further having the aperture communicate with a notch in which to secure the elastic member.

Another embodiment according to the present invention provides a snap-on clip having a head with a notch for receiving an elastic member therein. When the notch secures an elastic member, the tension from the elastic member aids the head of the snap-on clip to more securely engage the frame.

One embodiment according to the present invention provides for custom shaped variable geometry retractor frames made from extruded metal such as, for example, aluminum.

DETAILED DESCRIPTION OF INVENTION

According to the present invention a variable geometry retractor system provides a preformed custom shaped variable geometry retractor frame made from extruded materials and disposable snap-on clips for securing retractor stays. The variable geometry retractor system permits a surgeon to use a reduced number of prepackaged, sterilized snap-on clips with the variable geometry retractor frame. Also, the use of a variable geometry retractor frame permits the surgeon to place the snap-on clips around the retractor perimeter for improved placement of the snap-on surgical clips.

The frame of the variable geometry retractor may be formed from a single piece of extruded metal or from a plurality of extruded metal pieces. A variable geometry retractor frame prepared from a single piece of extruded metal may be bent into an appropriate shape which approximates a closed annular structure. The retractor frame may have the ends joined by, for example, welding, gluing, clamps or screws.

The frame or frame members can be prepared by machining cast or molded parts, but the preparation of frame and frame members by extrusion in a preshaped form has a cost advantage over machined parts. Machining, by lathe or milling machine, requires the manufacture of many copies of the same part to be cost effective. The metal bar stock used in the construction of the frames or frame members may be manufactured by extrusion. Extrusion manufacturing of metal bar stock is less expensive than machined stainless steel or aluminum bar stock leading to a reduction in cost for the frame and frame members. The extruded metal may be bent by, for example, using a combination of round dies and hydraulic presses, analogous to equipment used in a muffler shop to bend stock pipe into custom shaped pipes. The ease of modifying the combination of dies and presses to shape extruded metal permits the manufacture of low-cost variable geometry retractor frames even in small quantities.

Figure 1:
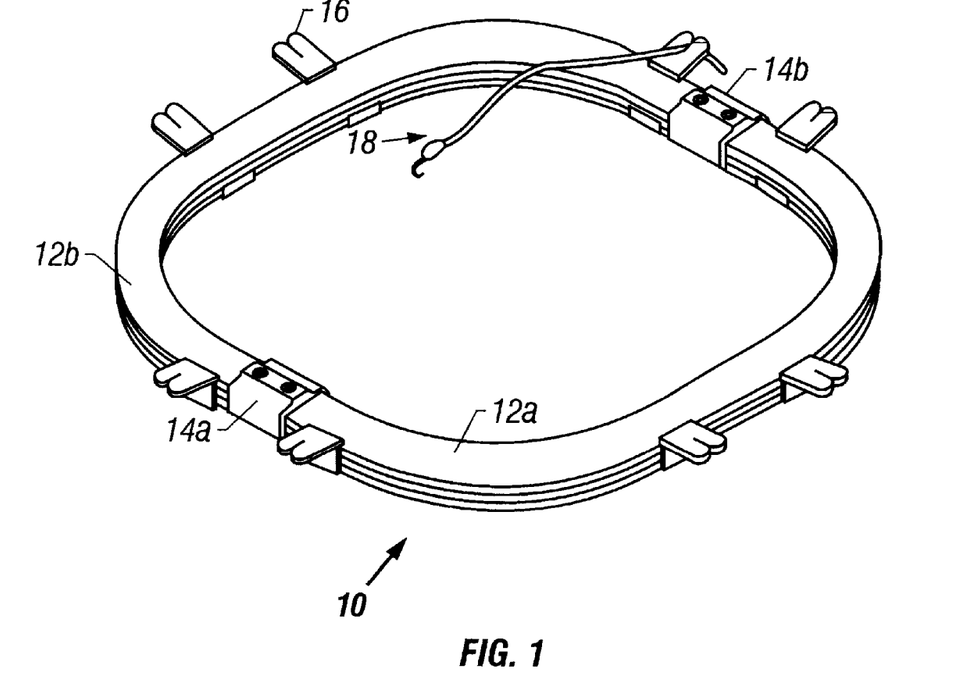
FIG. 1 is a perspective view of two rectangular frame members joined by couplers and having a series of snap-on clips with one retractor stay apparatus secured in a snap-on clip notch.

FIG. 1 shows one embodiment of the variable geometry retractor system according to the present invention having two retractor frame members 12a and 12b, frame member couplers 14a and 14b, snap-on clips 16 and a surgical retractor stay apparatus 18.

Figure 2:
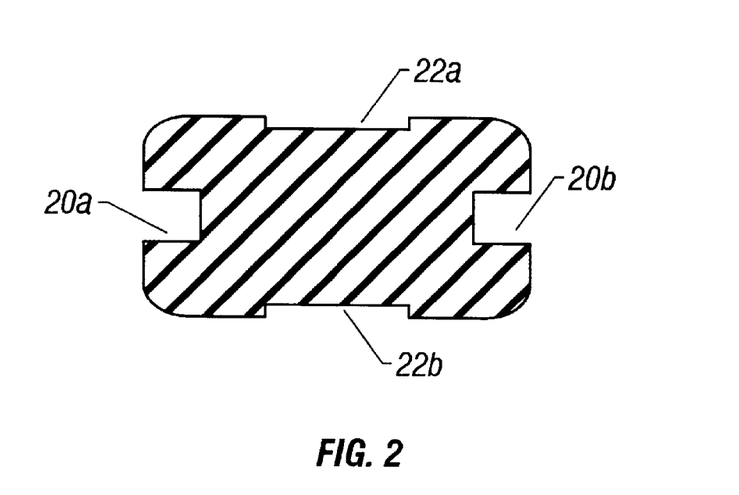
FIG. 2 is a sectional end view of a rectangular frame member showing parallel side tracks and upper and lower indentations.

In one illustrative system the frame members 12a and 12b in FIG. 1 are typically substantially rectangular as shown in FIG. 2. The frame members 12a and 12b have inner and outer parallel side tracks 20a and 20b, respectively. Frame members 12a and 12b also may have upper and lower parallel indentations 22a and 22b, respectively as shown in FIG. 2. The side tracks 20 and the upper and lower indentations 22 typically traverse the length of the frame member 12.

The inner and outer side tracks 20a and 20b permit the snap-on clip to be snapped onto the frame member 12 in any one of four orientations. These four orientations are combinations of the head 68 of the snap-on clip 16 being oriented either above or below the plane of the frame member 12 and being oriented toward the interior of the exterior of the assembled variable geometry frame.

The upper and lower indentations 22a and 22b receive the tightening element 34 from the frame member coupler 14. Having upper and lower indentations 22a and 22b permits the frame member coupler 14 to be attached to the frame member 12 such that the tightening element 34 may engage either the upper or lower indentation 22a or 22b. The indentations 22a and 22b also allow the tightening element 34 to seat onto the frame member 12 without exerting forces sufficient to deform the frame member 12. Deformation of the frame member 12 may impede the ability of the frame member coupler 14 to slide along the frame member 12. Further, any such deformation of frame member 12 may also impede the ability of the snap-on clips to move slidably along the length of frame member 12.

Figure 3:
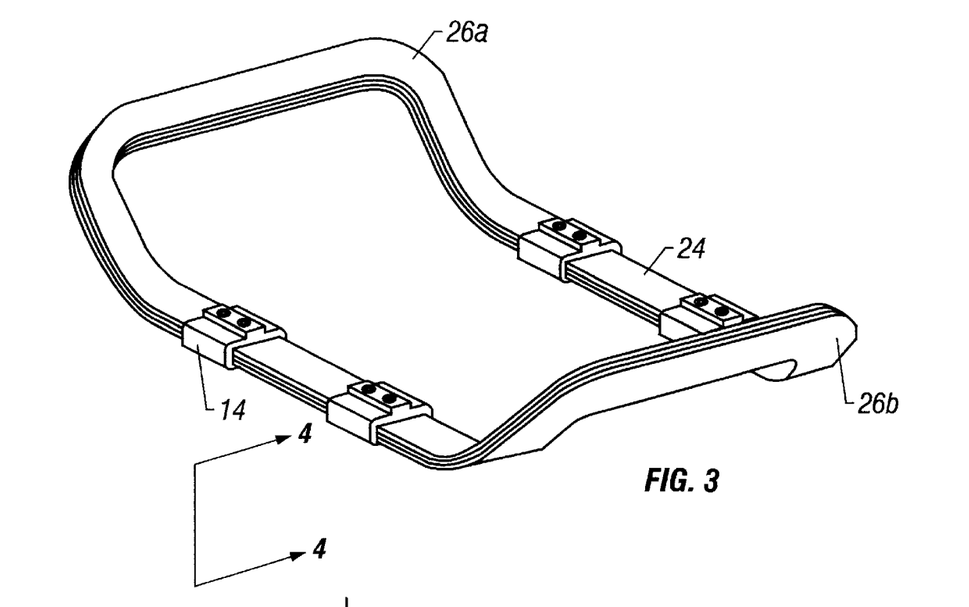
FIG. 3 is a perspective view of a variable geometry retractor frame having non-planar curved ends, extension members, and couplers.

FIG. 3 shows a second embodiment according to the present invention wherein the variable geometry retractor frame comprises both planar, straight frame members 24 and non-planar, curved frame members 26 which are bent relative to the plane formed by the straight frame members 24. The straight frame members 24 are typically coupled to the bent frame members 26 by a plurality of frame member couplers 14. The frame members 24 and 26, as shown in FIG. 3, also typically have side tracks 20 and upper and lower indentations 22. Alternatively, the frame in FIG. 3 could be made from a single piece of extruded metal, thereby eliminating the need for couplers.

Figure 4:
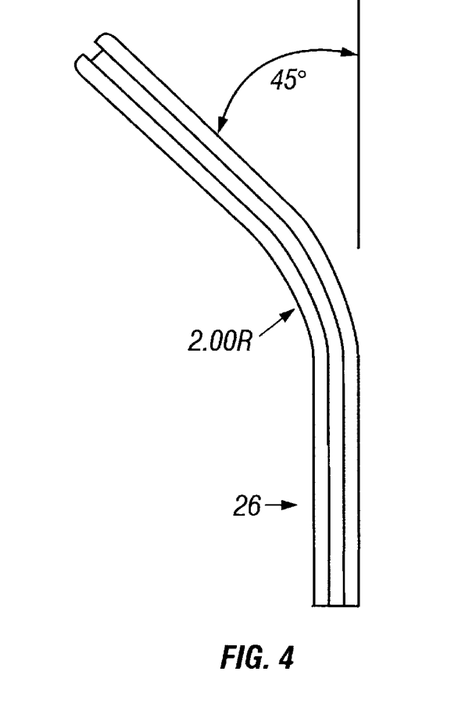
FIG. 4 is a side elevational view taken along lines 4—4 in FIG. 3.

FIG. 4 shows a side elevational view of the bent frame member 26 as viewed along lines 4—4 in FIG. 3. The bent frame member may typically be bent through an angle of from about 0 degrees to about 90 degrees. In one embodiment according to the invention the bent frame member 26 has a bend of about 45° with respect to the plane of the straight frame members. The use of the straight frame members 26 between curved frame members 12 or bent frame members 26 permits the construction of a variable geometry retractor frame for use with large surgical incision sites or for larger patients. An appropriate combination of curved frame members 12, straight frame members 24, and bent frame members 26 permits a surgeon to construct a three-dimensional variable geometry retractor whose frame better conforms to a patient's body at a surgical site.

Figure 5:
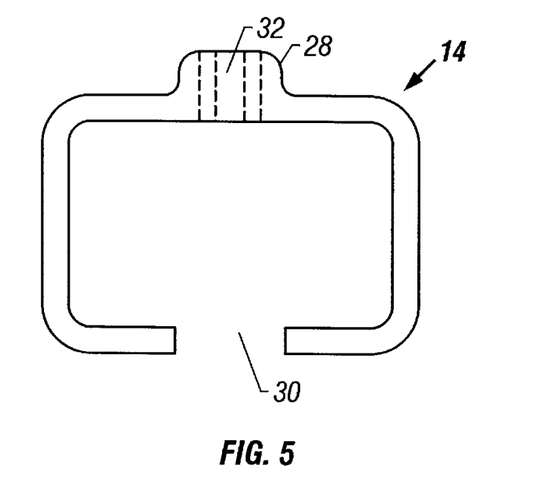
FIG. 5 is an end elevational view of a coupler for a rectangular frame member.
Figure 6:
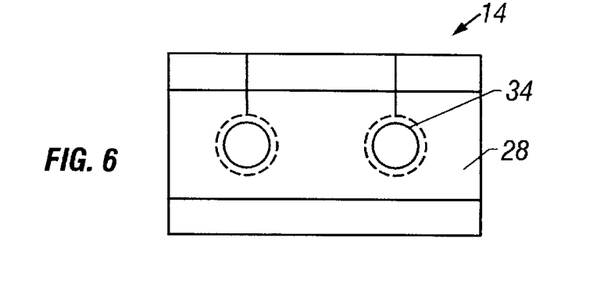
FIG. 6 is a plan view of the coupler for a rectangular frame member showing the tightening elements.

The frame member couplers 14 are sized and shaped to approximate the size and shape of a corresponding frame member 12. The shapes of the frame members include, but are not limited to, tubular, cylindrical, rod-like, rectangular and square. One embodiment according to the invention of the frame member couplers 14, for use with frame members 12, 14 and 26, as shown in FIGS. 1–4, is shown in FIGS. 5 and 6. FIG. 5 is an end elevational view of the frame member coupler 14. The frame member coupler 14 shown in FIGS. 5 and 6 is approximately rectangular in shape and is sized and shaped to slidably receive the ends of two frame members 12, 24, or 26 as shown in FIG. 2. The frame member coupler 14 has a ridge 28 on one surface and a gap 30 the length of the coupler in an opposing side, as shown in FIG. 5. The frame member coupler 14 alternatively may be made without the gap 34. Having the gap 30 provides an economic benefit in that a frame member coupler 14 having a gap 30 may be made by an extrusion process with a less expensive die. The ridge 28 has a plurality of recesses 32 for receiving a tightening element 34 such as set screws. The tightening elements 34 are used to reversably engage the top indentation 22 on the frame members 12 to secure frame members 12, 24 or 26 for use in a surgical procedure. The frame member couplers 14 may then be disengaged from the frame members 12, 24, or 26 after the surgical procedure to permit disassembly of the variable geometry retractor frame for cleaning and sterilization when re-use of the retractor frame is desired. The lower cost due to construction of the retractor frame from extruded metal pieces may make disposable of the retractor frame competitive with the cost of disassembling, sterilizing and reassembling the retractor frame.

Figure 15:
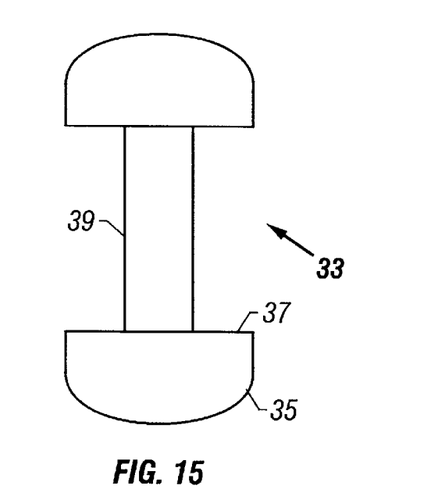
FIG. 15 is a side elevational view of a plug.
Figure 16:
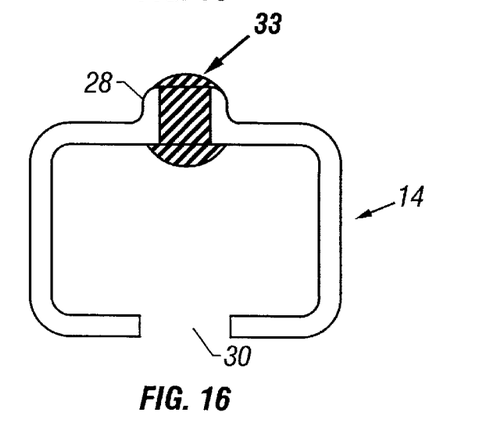
FIG. 16 is a side elevational view of a plug inserted into a coupler for a rectangular frame.

An alternative tightening element 34 may be, for example, a double headed plug 33 made from a flexible material. The plug may have two hemispherical heads each having a flat inner surface 37. The two hemispherical heads 35 are connected by a connector 39 which may be made from the same flexible material, a different flexible material or even a non-flexible material. The plug 33 is inserted into recess 32 of frame member coupler 14. The connector 39 of the plug is of such length that it permits one head 35 of the plug 33 to be inserted completely through the recess and into the interior portion of the frame member coupler 14. The diameter of the two head 35 portions of the plug 33 exceeds the diameter of the recess 32. The plug 33 is made of a resilient material so that the head 35 inserted to the recess may be deformed to allow passage through the recess 32 and then expand to its original shape to prevent the plug from easily pulling out of recess 32. The remaining plug head 35 remains external to the frame member coupler 14. The diameter of the head 35 of the plug 33 prevents the plug from falling completely through recess 32. The plug head 35 in the interior of the frame member coupler 14 engages one of the indentations 22 on the frame member 12 to secure the frame member for use in a surgical procedure. The plug 33 may be made of any flexible, resilient material capable of being deformed during the insertion process and capable of substantially returning to its original shape after insertion. Silicone rubber is one example of an acceptable flexible material.

Figures 7, 8:
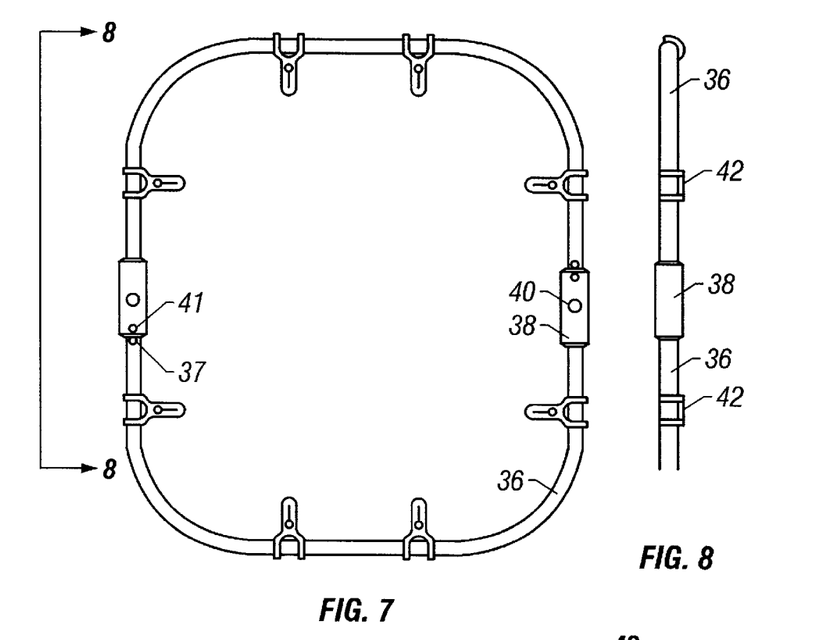
FIG. 7 is a plan view of two cylindrical, semi-circular frame members joined by couplers and a plurality of snap-on clips affixed thereto.
FIG. 8 is a side elevational view taken along lines 8—8 of FIG. 7 showing the snap-on clips and coupler on the cylindrical frame.

FIG. 7 shows another embodiment according to the present invention in which the variable geometry retractor frame has cylindrical, tubular or rod shaped frame members 36 which are curved and generally U-shaped. Cylindrical frame member couplers 38 secure two cylindrical frame members 36 to form an annular variable geometry retractor stay system 10. As shown FIG. 7, the cylindrical frame member coupler 38 receives one end of each of two cylindrical frame members 36.

In one embodiment according to the present invention the cylindrical frame member coupler 38 has left-hand threads inside a portion of one end of the coupler 38 and has right-hand threads inside a portion of the other end of the coupler 38. A frame member 36 to be used with a frame member coupler 38 will have left-hand threads on one end of the frame member 36 and right-hand threads on the other end of the frame 36. Both the frame 36 and the frame member coupler 38 may have dimples or other markings or indicators denoted 37 and 41, respectively to indicate the frame ends having either the left-hand or right-hand threads to aid rapid assembly. The frame member coupler 38 may also have a through-hole 40 to permit the use of a spanner wrench to tighten the frame member coupler 38 sufficiently to secure the frame members 36. Alternative embodiments include frame member couplers 38 with a smooth bore and sized to receive the frame member 36 and hold it in place through frictional forces. Other alternative embodiments include frame member couplers 38 and frame members 36 having corresponding holes to permit the use of securing devices such as screws or pins.

FIG. 7 further shows the snap-on clips snapped onto the cylindrical frame member 36. FIG. 8 shows a side elevational view along the lines 8—8 in FIG. 7 of a portion of two cylindrical frame members 36 connected by a cylindrical frame member coupler 38 with snap-on clips snapped onto the cylindrical frame members 36. As shown in FIG. 7, the snap-on clips may be placed by the surgeon at points on the cylindrical variable geometry frame member which afford the desired positions for the snap-on clips and the retractor stays. Using the snap-on clips, the surgeon is not limited to securing the retractor stay in an unmovable, prepositioned notch integrally formed in the retractor frame.

The frame can be made from a light weight metal, for example aluminum. Light weight metal construction permits easy cleaning and re-sterilization at the hospital facilities or autoclaving in the operating room.

Further, the retractor frames can be easily pre-formed at the factory. This permits the construction of frames having custom three-dimensional shapes as determined by surgeons for specific surgical procedures. The use of custom designed, pre-fabricated retractor frames helps to reduce or eliminate assembly and setup time of the retractor system prior to surgery.

The snap-on clips are for use with a surgical retractor frame and a retractor stay apparatus having an elastic member. The snap-on clip includes a body having a recess connected to a head having a notch. The snap-on clips may have the head and body integrally formed by, for example, a molding process. The recess is sized and shaped to snap onto a surgical retractor frame. The surgical retractor frame may be either a conventional retractor frame or a variable geometry retractor frame. The notch is sized and shaped to secure the elastic member of a retractor stay apparatus.

Figure 10:
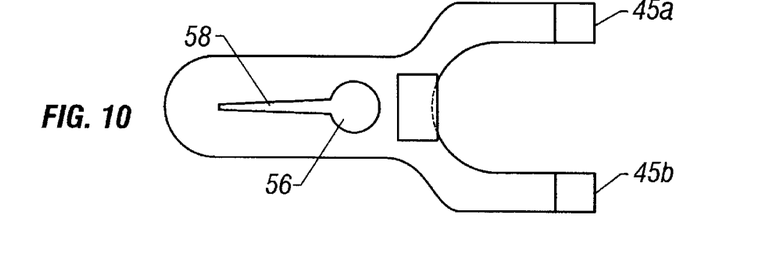
FIG. 10 is a plan view of a snap-on clip for a cylindrical frame.
Figure 11:
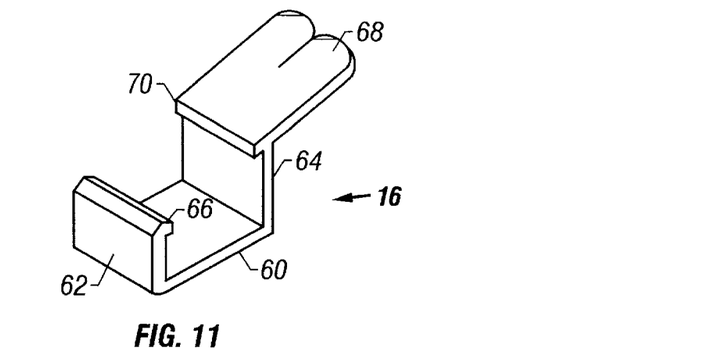
FIG. 11 is a perspective view of the snap-on clip for a rectangular frame.
Figure 12:
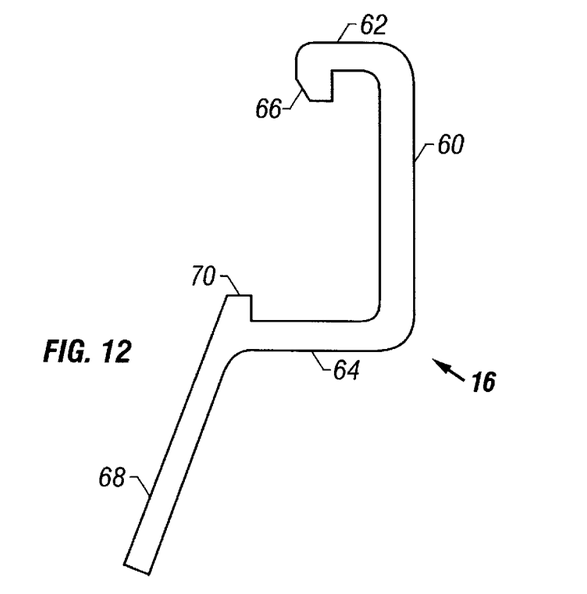
FIG. 12 is a side view of a snap-on clip for a rectangular frame.

The snap-on clips, shown in FIGS. 10, 11 and 12, are made of flexible materials capable of allowing a recess in the snap-on clip to receive a frame member. The flexible materials include, but are not limited to, materials such as plastics including poly(phenylene oxide) (sold by General Electric under the trademark NORYL), nylon and polycarbonate. The snap-on clips may also be made of flexible non-plastic materials such as, for example, stamped spring metal which has sufficient flexibility to allow the metal snap-on clip to snap onto the frame. The metal snap-on clip may be made out of any durable metal having sufficient flexibility to snap onto a frame which would include, for example, stainless steel. The metal snap-on clips may also be disposable or reuseable. Reuseable metal snap-on slips may be sterilized by methods that would be detrimental to the integrity of some plastic snap-on clips.

Figure 9:
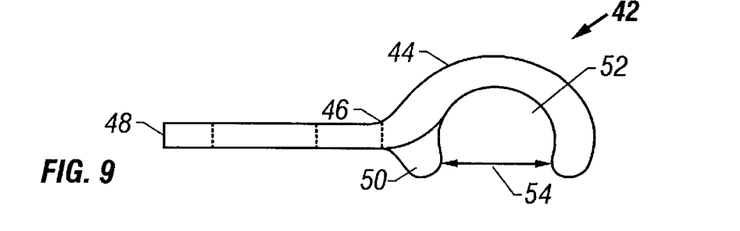
FIG. 9 is a side elevational view of a snap-on clip for a cylindrical frame.

One embodiment of the snap-on clips 42 according to the invention, as shown in FIGS. 9 and 10, has a proximal end 44, a transition point 46 and a distal end 48. The proximal end 44 is arc-shaped and, in conjunction with the knob 50, forms a recess 52 for receiving a portion of a cylindrical frame member 36. The opening 54 formed by the knob 50 and the end of the arc-shaped proximal end 44 of the snap-on clip 42 is less than the diameter of the cylindrical frame member 36. The arc-shaped proximal end 44 is flexible enough to allow dislocation of the arc-shaped proximal end 44 to permit the opening 54 to widen sufficiently to receive the cylindrical frame member 36. The recess 52 is sized such that after receiving the cylindrical frame member 36 the end of the arc-shaped proximal end 44 and the knob 50 engage the cylindrical frame member 36 preventing its accidental disengagement while permitting the surgeon to slidably adjust the snap-on clip 42 along the length of the cylindrical frame member 36.

FIG. 10 shows one embodiment according to the invention of the snap-on clip 42. The distal end of the snap-on clip 42 has an aperture 56 near the transition point 46. A notch 58 extends from the aperture 56 in a direction generally distal to the proximal end of the snap-on clip 42. The aperture 56 is sized so as to be able to receive an elastic member from a surgical retractor stay apparatus. The notch 58 is typically approximately the width of the elastic member of a surgical retractor stay apparatus at the point at which the notch 58 communicates with the aperture 56. The notch 58 is typically tapered to a decreasing width such that as the elastic member is inserted further into the notch an increasing frictional force is applied to the elastic member to secure the elastic member. This prevents accidental disengagement of the elastic member from the notch 58 while permitting the surgeon to easily remove the elastic member from the notch 58 to adjust tension on the elastic member.

Figure 14:
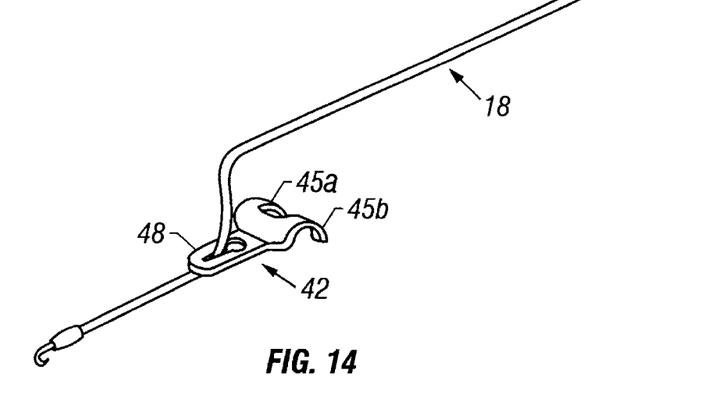
FIG. 14 is a perspective view of a snap-on clip for a cylindrical frame member wherein the elastic member of a surgical stay apparatus is engaged in the snap-on clip notch.

In one embodiment according to the present invention as shown in FIGS. 10 and 14, the proximal end 44 of the snap-on clip 42 is bifurcated providing two arc-shaped arms 45*a* and 45*b*. Alternatively, the proximal end 44 may be a single arc-shaped arm or a plurality of arc-shaped arms.

Figure 13:
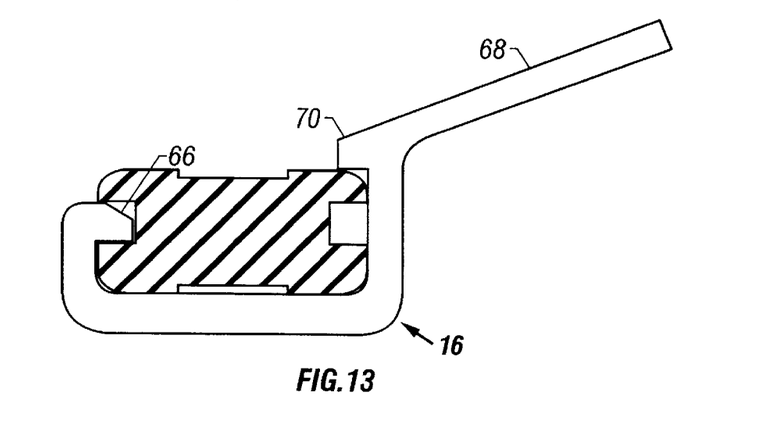
FIG. 13 is a sectional side view of a snap-on clip for a rectangular frame member showing engagement of the frame member in the snap-on clip.

FIGS. 11, 12, and 13 show another embodiment of the snap-on clip according to the present invention. The snap-on clip 16 has a generally U-shaped body having a base 60, a first wall 62, and a second wall 64, wherein the first wall 62 and second wall 64 are affixed to opposite sides of the base 60. The first wall 62 has a lip 66 which extends over a portion of the base 60. As shown in FIG. 13, the first wall 62 is sized so as to position the lip 66 to engage a side track 20 of a frame member 12. The lip 66 is sized so as to securely but reversibly engage the frame member 12 by insertion into the side track 20. The second wall 64 has a head 68 with a body member extending at least a sufficient portion of the width of the second wall 64 to permit a notch 72 to be formed in the body member. The body member may have any shape capable of having a notch to receive an elastic member.

In one embodiment according to the invention, the body member has a plate-like body. The head 68 has a lip 70 extending over part of the base 60. The head lip 70 engages the top side of the frame member 12 and, in cooperation with lip 66 engaged in the side track 20, securely engages the snap-on clip 16 onto the frame member 12, 24 or 26. The body member portion of the head 68 and includes a notch 72 for receiving the elastic member of a surgical retractor stay apparatus. When an elastic member is secured in notch 72, the tension exerted by the elastic member increases the force with which head lip 70 engages the top side of frame member 12. This increased pressure, due to the elastic member, by which head lip 70 engages the frame member 12 aids the head of the snap-on clip to more securely engage the frame. The head 68 is angled relative to the wall 64 so as to permit the surgeon to easily insert and remove an elastic member from the notch 72. The snap-on clip 16 may also be slidably adjustable along the length of the fame member.

One method according to the present invention of retracting tissue at an incision during surgery includes the steps of: (a) applying a retractor frame conformed to fit a surface of the patient's body; (b) snapping a sterilized snap-on clip including a notch onto the frame; (c) attaching a surgical retractor stay having an elongated elastic member with a width and proximal and distal ends and a tissue holding member, the tissue holding member affixed to the proximal end of the elastic member by inserting a portion of the distal end of the elongated elastic member into the notch on the snap-on clip and engaging tissue with the tissue holding member; (d) removing the stay, frame and snap-on clip after completing the surgical procedure; (e) disposing of the snap-on clip; and (f) sterilizing the frame for reuse. The method may include the optional steps of (1) disassembling the frame prior to sterilization and (2) reassembling the frame after sterilization. The retractor frame in step (a) includes both conventional retractor frames and variable geometry retractor frames.

Thus, according to the present invention a variable geometry retractor system provides a preformed annular retractor frame, which may be non-planar, and disposable snap-on clips. The variable geometry retractor system permits a surgeon to use a reduced number of prepackaged, sterilized snap-on retractor stay clips with the variable geometry retractor frame. The use of snap-on clips with the variable geometry retractor frame permits the surgeon to place the snap-on clip at a desired location on the retractor perimeter.

The foregoing disclosure and description of the invention are illustrative and explanatory thereof, and various changes in the details of the illustrated apparatus and construction and method of operation may be made without departing from the spirit of the invention.

What is claimed is:

1. A surgical retractor stay system comprising:
   a) a frame adapted to engage at least one snap-on clip, the frame comprising a plurality of frame members each having a first end and a second end, and a plurality of couplers having a first end opening and a second end opening, each opening receiving the first end or second end of the frame members; and
   b) a snap-on clip having a recess to receive the frame and having a notch for securing an elastic member having a width.

2. The surgical retractor stay system of claim 1, wherein the snap-on clip further comprises:
   a) a body, having the recess, connected to a head having the notch;
   b) the recess being sized and shaped to snap onto the surgical retractor frame; and
   c) the notch being sized and shaped to secure the elastic member.

3. The surgical retractor stay system of claim 2 wherein the recess is adapted to receive a variable geometry retractor frame.

4. The surgical retractor stay system of claim 3 wherein the recess is rectangular.

5. The surgical retractor stay system of claim 4 wherein securing the elastic member in the notch aids the head of the snap-on clip to more securely engage the frame.

6. The surgical retractor stay system of claim 5 wherein the flexible material is selected from the group consisting of poly (phenylene oxide), nylon, polycarbonate and stamped metal.

7. The surgical retractor stay system of claim 3 wherein the recess is semi-circular.

8. The surgical retractor stay system of claim 2 wherein the head and body are integrally formed.

9. The surgical retractor stay system of claim 2 wherein the snap-on clip is made from a flexible material.

10. The surgical retractor system of claim 1, wherein the snap-on clip is slidably movable on the frame.

11. The surgical retractor system of claim 1, wherein the frame is made from extruded metal.

12. The surgical retractor system of claim 11, wherein the extruded metal is aluminum.

13. The surgical retractor stay system of claim 1 wherein:
  a) the frame is cylindrical; and
  b) the snap-on clip has a distal end, an arcuate proximal end and a knob, the proximal end and the knob defining the recess of the snap-on clip.

14. The surgical retractor stay system of claim 13 wherein the distal end of the snap-on clip has an aperture communicating with the notch, the aperture being sized and shaped e receive an elastic member of a surgical retractor stay.

15. The surgical retractor stay system of claim 14 wherein the notch is tapered to a width less than the width of the elastic member.

16. The surgical retractor stay system of claim 1 wherein:
  a) the frame members are rectangular having an inner and outer side, the sides having indented tracks and
  b) the snap-on clip comprises:
    1) a body having a base, a first wall, and a second wall wherein the first wall and second wall are affixed to the base, the walls and the base form a rectangular recess;
    2) a lip on the first wall extending over the base;
    3) a head having a lip and a body member on the second wall, the lip of the head extending over the base and the body member extending away from the base; and
    4) the body member having a notch for receiving the elastic member.

17. The surgical retractor stay system of claim 16, wherein the body member is plate-like.

18. The surgical retractor stay system of claim 16, wherein the wall lip and the head lip detachably engage the frame member tracks.

19. The surgical retractor stay apparatus of claim 16 wherein the notch is tapered to a width less than the width of the elastic members.

20. The surgical retractor stay apparatus of claim 16 wherein the snap-on clip is slidably movable along the frame.

21. A method of retracting tissue at an incision during surgery upon a portion of a patient's body at a surgical site, comprising the steps of:
  (a) applying a frame conformed to fit a surface of the patient's body;
  (b) snapping a snap-on clip having a notch onto the frame;
  (c) attaching a surgical retractor stay having an elastic member with a width, a distal end and a proximal end having a tissue holding member, by inserting the distal end of the elastic member into the notch on the snap-on clip and engaging tissue with the tissue holding member;
  (d) removing the stay, frame and snap-on clip after completing the surgical procedure;
  (e) disposing of the snap-on clip; and
  (f) sterilizing the frame for reuse.

22. The method of claim 21 wherein the frame is an extruded metal.

23. The method of claim 21 wherein the frame comprises:
  a) a plurality of metal frame members adapted to engage at least one snap-on clip, the frame members each having a first end and a second end; and
  b) a plurality of couplers having a first end opening and a second end opening, each opening receiving the first end or second end of a frame member.

24. The method of claim 21 wherein:
  a) the frame is cylindrical; and
  b) the snap-on clip has a distal end, an arcuate proximal end and a knob, the proximal end and the knob defining the recess of the snap-on clip.

25. The method of claim 21 wherein the distal end of the snap-on clip has an aperture communicating with the notch, the aperture being sized and shaped to receive the elastic member.

26. The method of claim 21 wherein the notch is tapered to a width less than the width of the elastic member.

27. The method of claim 21 wherein:
  a) the frame is rectangular having an inner and outer side, the sides having indented tracks and
  b) the snap-on clip comprises:
    1) a body having a base, a first wall, and a second wall wherein the first wall and second wall are affixed to the base, the walls and base forming a rectangular recess;
    2) a lip on the first wall extending over the base;
    3) a head having a lip and a body member on the second wall, the lip of the head extending over the base and the body member extending away from the base; and
    4) the body member having a notch for receiving the elastic member.

28. The method of claim 27 wherein the body member is plate-like.

29. The method of claim 27 wherein the wall lip and the head lip detachably engage the frame tracks.

30. The method of claim 27 wherein the notch is tapered to a width less than the width of the elastic members.

31. The method of claim 27 wherein the snap-on clip is slidably movable along the frame tracks.

32. A method of retracting tissue at an incision during surgery upon a portion of a patient's body at a surgical site, comprising the steps of:
  (a) applying a frame conformed to fit a surface of the patient's body;
  (b) snapping a snap-on clip having a notch onto the frame;
  (c) attaching a surgical retractor stay having an elastic member with a width, a distal end and a proximal end having a tissue holding member, by inserting the distal end of the elastic member into the notch on the snap-on clip and engaging tissue with the tissue holding member; and
  (d) removing the stay, frame and snap-on clip after completing the surgical procedure.

* * * * *